(12) United States Patent
Bernhardt et al.

(10) Patent No.: US 8,041,096 B2
(45) Date of Patent: Oct. 18, 2011

(54) METHOD FOR CREATING MASS DENSITY IMAGES ON THE BASIS OF ATTENUATION IMAGES CAPTURED AT DIFFERENT ENERGY LEVELS

(75) Inventors: Philipp Bernhardt, Forchheim (DE); Ernst-Peter Rührnschopf, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 806 days.

(21) Appl. No.: 12/148,791

(22) Filed: Apr. 22, 2008

(65) Prior Publication Data

US 2010/0027867 A1 Feb. 4, 2010

(30) Foreign Application Priority Data

Apr. 27, 2007 (DE) .................. 10 2007 020 065

(51) Int. Cl.
*G06K 9/00* (2006.01)
*G01N 23/04* (2006.01)
(52) U.S. Cl. ..................... 382/132; 382/128; 378/62
(58) Field of Classification Search .......... 382/128, 382/132; 378/62
See application file for complete search history.

(56) References Cited

U.S. PATENT DOCUMENTS

| | | | |
|---|---|---|---|
| 4,217,641 A | | 8/1980 | Naparstek |
| 4,247,774 A | * | 1/1981 | Brooks .................. 250/367 |
| 5,115,394 A | * | 5/1992 | Walters .................. 382/131 |
| 5,164,590 A | * | 11/1992 | Coles et al. ............... 250/255 |
| 6,104,777 A | * | 8/2000 | Darboux et al. .......... 378/62 |
| 6,175,755 B1 | * | 1/2001 | Hogg et al. ............... 600/407 |
| 6,636,622 B2 | * | 10/2003 | Mackie et al. ............ 382/132 |
| 7,050,533 B2 | * | 5/2006 | Heismann et al. ........ 378/53 |
| 7,065,234 B2 | * | 6/2006 | Du et al. .................. 382/131 |
| 7,092,485 B2 | * | 8/2006 | Kravis ..................... 378/57 |
| 7,352,887 B2 | * | 4/2008 | Besson .................... 382/132 |
| 7,469,037 B2 | * | 12/2008 | Wernick et al. ........... 378/82 |
| 2003/0128801 A1 | * | 7/2003 | Eisenberg et al. ........ 378/19 |
| 2004/0223585 A1 | | 11/2004 | Heismann et al. |

FOREIGN PATENT DOCUMENTS

| | | |
|---|---|---|
| DE | 2916486 A1 | 10/1979 |
| DE | 4410888 A1 | 10/1995 |
| DE | 10143131 A1 | 4/2003 |

OTHER PUBLICATIONS

Warp et al., "Quantitative evaluation of noise reduction strategies in dual-energy imaging", Medical Physics, Feb. 2003, pp. 190-198, vol. 30, No. 2.
Zellerhoff et al., "Low contrast 3D reconstruction from C-arm data" Proceedings of SPIE, Medical Imaging 2005, pp. 646-655, vol. 5745.
Cullen et al., "EPDL97: The Evaluated Photon Data Library '97 Version", Lawrence Livermore National Laboratory, Sep. 19, 1997, pp. 1-34, UCRL-ID-50400, vol. 6, Rev. 5.

(Continued)

*Primary Examiner* — Andrew W Johns
*Assistant Examiner* — Shefali Goradia

(57) ABSTRACT

The invention relates to a method for creating scatter-corrected mass density image in dual energy X-ray absorptiometry. The mass density image is created using additional information provided by attenuation images at different energy levels in an inhomogeneous correction image area. A multi-dimensional mass density is found that is consistent for a plurality of the attenuation images by inverting a primary radiation function. A scatter fraction is determined on the basis of the multi-dimensional mass density.

18 Claims, 5 Drawing Sheets

OTHER PUBLICATIONS

International Commission on Radiation Units and Measurements, "Tables of X-Ray Mass Attenuation Coefficients and Mass Energy-Absorption Coefficients", Tissue substitutes in radiation dosimetry and measurement,Report 44, 1989, pp. 1-5.

Floyd Jr. et al., "Posterior Beam-Stop Method for Scatter Fraction Measurement in Digital Radiography", Investigative Radiology, Feb. 1992, pp. 119-123, vol. 27, No. 2.

Press et al., "Numerical Recipes—The Art of Scientific Computing / (FORTRAN Version)", 1989, pp. 268-273; Cambridge University Press; 052138330-7.

Hinshaw et al., "Recent progress in noise reduction and scatter correction in dual-energy imaging", 1995, pp. 134-142, Proc. SPIE vol. 2432.

* cited by examiner

METHOD FOR CREATING MASS DENSITY IMAGES ON THE BASIS OF ATTENUATION IMAGES CAPTURED AT DIFFERENT ENERGY LEVELS

CROSS REFERENCE TO RELATED APPLICATIONS

This application claims priority of German application No. 10 2007 020 065.1 filed Apr. 27, 2007, which is incorporated by reference herein in its entirety.

FIELD OF THE INVENTION

The invention relates to a method for creating mass density images on the basis of attenuation images captured at different energy levels.

BACKGROUND OF THE INVENTION

A method of this kind is known from WARP, R. J.; DOBBINS, J. T.: Quantitative evaluation of noise reduction strategies in dual-energy imaging, in: Med. Phys. 30 (2), pages 190 to 198, February 2003. In the context of dual energy X-ray absorptiometry, X-ray beams with differing energy levels are directed at the examination subject, generally a patient. Dual energy X-ray absorptiometry can be accomplished using a single X-ray shot or a series of consecutively taken shots.

In the first case, a dual detector is used which incorporates two different scintillation materials whose response has energy centers that are as far apart as possible. In the second case, consecutive shots are taken using as differing X-ray spectra as possible which, when using X-ray tubes, can be generated by varying the tube voltage by means of which the electrons are accelerated, or by selecting pre-filters.

For each pixel of the projection images recorded, the material composition in the beam path between the point X-ray source and the pixels can be inferred from the attenuation behavior at the different energy levels. The projection images will hereinafter also referred to as attenuation images. Material composition is also to be understood as the mass density of the different materials along the beam through the examination subject.

By combining the attenuation images captured at different energy levels, mass density images can be created which render, at least approximately, the mass density of the materials contained in the subject examined. The attenuation images are usually combined linearly, the weighting factors being determined empirically. However, mathematically precise determination of the mass density is virtually impossible using the known methods.

Mathematically precise determination of mass density is also made more difficult by the scattered radiation present. Even in projection radiography using flat panel detectors, scattered radiation plays a critical role because of the large solid angle detected. To reduce the scattered radiation, anti-scatter grids are frequently inserted directly above the detector input surface. As a quantitative method, dual energy X-ray absorptiometry places more exacting requirements again on the accuracy of the measurement data than simple projection imaging in the context of projection radiography. In spite of anti-scatter grids, the data-distorting scatter fraction may be considerable. For example, in the thorax area a very small air gap is usually employed, with the result that in spite of anti-scatter grids the scatter intensity may if anything outweigh the primary intensity, particularly in image regions with high attenuation and at higher photon energies, corresponding to X-ray tube voltages above 100 kV. Moreover, it is an empirical fact that scatter fractions are very different for the higher and lower energy image data, particularly in the case of a small air gap, i.e. where the distance between the scatter object and the detector is small. All in all, in dual energy X-ray absorptiometry the presence of scattered radiation may, in spite of anti-scatter grids, yield unreliable and in some cases unusable results, e.g. negative material thicknesses. Scatter correction is therefore of major importance for dual energy X-ray absorptiometry.

With dual energy X-ray absorptiometry, it is therefore necessary to use computerized scatter correction methods in addition to anti-scatter grids.

It should be noted at this point that scattered radiation will hereinafter also be referred to as secondary radiation. The sum of primary and secondary radiation which produces the measured image values will be termed total radiation.

HINSHAW, D. A.; DOBBINS III, J. T.: Recent progress in noise reduction and scatter correction in dual-energy imaging. In: Proc. SPIE, 1995, Vol. 2432, pages 134 to 142, describe a scatter correction method in the context of dual energy X-ray absorptiometry. In the known method, for each of the attenuation images captured at different energy levels, scatter correction is performed by determining for a given pixel an empirically calculated scatter fraction as a function of the pixel. The scatter fraction determines the shape and width of a distribution function for the scattered radiation. On the basis of the scatter function, the scatter contributions in adjacent pixels are calculated. The method is then repeated for further image values and the scatter contributions in the individual pixels are summed. A convolution of the image registered by the detector device with a distribution function therefore takes place, the width and shape of which depend on the image values of the attenuation image captured by the detector device.

FLOYD, C. B.; BAKER, J. A.; LO, J. Y.; RAVIN, C. E: Posterior Beam-Stop Method for Scatter Fraction Measurement in Digital Radiography. In: Investigative Radiology Feb. 1992, Vol. 27, pages 119 to 123, describe a measurement-based method for determining scattered radiation according to the beam-stop method. This method is suitable for laboratory applications using phantoms, but hardly for clinical use.

In addition, ZELLERHOFF, M.; SCHOLZ, B.; RÜHRNSCHOPF, E.-P.; BRUNNER, T.: Low contrast 3D-reconstruction from C-arm data. In: Proceedings of SPIE. Medical Imaging, 2005, Vol. 5745, pages 646 to 655, describe various computerized methods for scatter correction in the context of computed tomography.

However, the known computerized methods are generally quite complex and laborious.

Moreover, there therefore exists a need for comparatively simple correction methods enabling significant image quality improvements to be achieved.

SUMMARY OF THE INVENTION

On the basis of this prior art, the object of the invention is therefore to specify a method with which mass density images of improved quality compared to the prior art can be produced.

This object is achieved by a method having the features set forth in the independent claims. Advantageous embodiments and further developments are detailed in claims dependent thereon.

The method comprises the following steps:
- generating radiation using a radiation source and X-raying an examination subject by means of the radiation;
- applying the radiation to a detector device and acquiring attenuation images at different energy levels by means of the detector device; and
- determining mass density images by means of a processing unit connected downstream of the detector device.

With the method, the values for the mass density in the subject are determined by inverting a multi-dimensional attenuation function. As the attenuation function links multi-dimensional mass density in the subject with attenuation values of the attenuation images captured at different energy levels, the associated mass density image can be determined from the attenuation images by inversion of the multi-dimensional attenuation function. As the attenuation values are monotonically dependent on the mass density values and the attenuation values scale nonlinearly with the energy of the radiation used, there always exists a unique solution to the inversion problem. In this respect the mass density of the components present in the subject can be precisely determined. The method is ultimately based on a consistency condition, namely that inversion of the multi-dimensional attenuation function must necessarily produce consistent mass densities, as the attenuation images captured at different energy levels reproduce the same subject in each case.

In a preferred embodiment of the method, a secondary radiation fraction caused by scatter is determined and the attenuation images are corrected in respect of the secondary radiation fraction to a primary radiation fraction produced by attenuation. This enables the quality of the mass density images produced by inversion of the multi-dimensional attenuation function to be significantly improved, as the results are not distorted by the secondary radiation fractions.

In another preferred embodiment of the method, in order to determine the secondary radiation fractions of the attenuation images captured at different energy levels, those secondary radiation fractions are found which are linked to primary attenuation fractions which yield the same mass density for the correction image area in each case when the inverse multi-dimensional attenuation function is evaluated. As the secondary radiation fractions depend on the mass density and the mass density in turn depends on the primary attenuation fractions which are only produced when the measured image values are corrected in respect of the secondary radiation fractions, implicit equations emerge whose solution must be determined by a search process. The search process is usually performed by means of an iteration which enables the implicit equations to be solved.

In another preferred embodiment of the method, the secondary radiation fractions in a correction area which maps an inhomogeneous region of the subject are determined by inverting a multi-dimensional attenuation function which depends on multi-dimensional mass densities. The result of inversion is a multi-dimensional mass density with which the attenuation structure of the examination subject can be determined at least to an approximation. On the basis of the multi-dimensional mass density, the secondary radiation fraction can be determined at least approximately.

The secondary radiation fraction is preferably determined by convolving a convolution function dependent on the multi-dimensional mass density with the determined primary attenuation fraction in the attenuation images.

It is also possible, using Monte Carlo simulation, to determine the particular secondary radiation fraction. The Monte Carlo simulation can be performed in advance and the results tabulated as a function of multi-dimensional mass densities.

Scatter correction can be performed on individual pixels of the attenuation image or determined on the basis of image values averaged over a predefined area. The secondary radiation fraction is preferably determined in the region of data points of a grid placed over the attenuation image and the secondary radiation fraction is interpolated for pixels between the data points.

BRIEF DESCRIPTION OF THE DRAWINGS

Other characteristics and advantages of the invention will emerge from the following description in which examples of the invention are explained in detail with reference to the accompanying drawings in which.

DETAILED DESCRIPTION OF THE INVENTION

Figure 1:
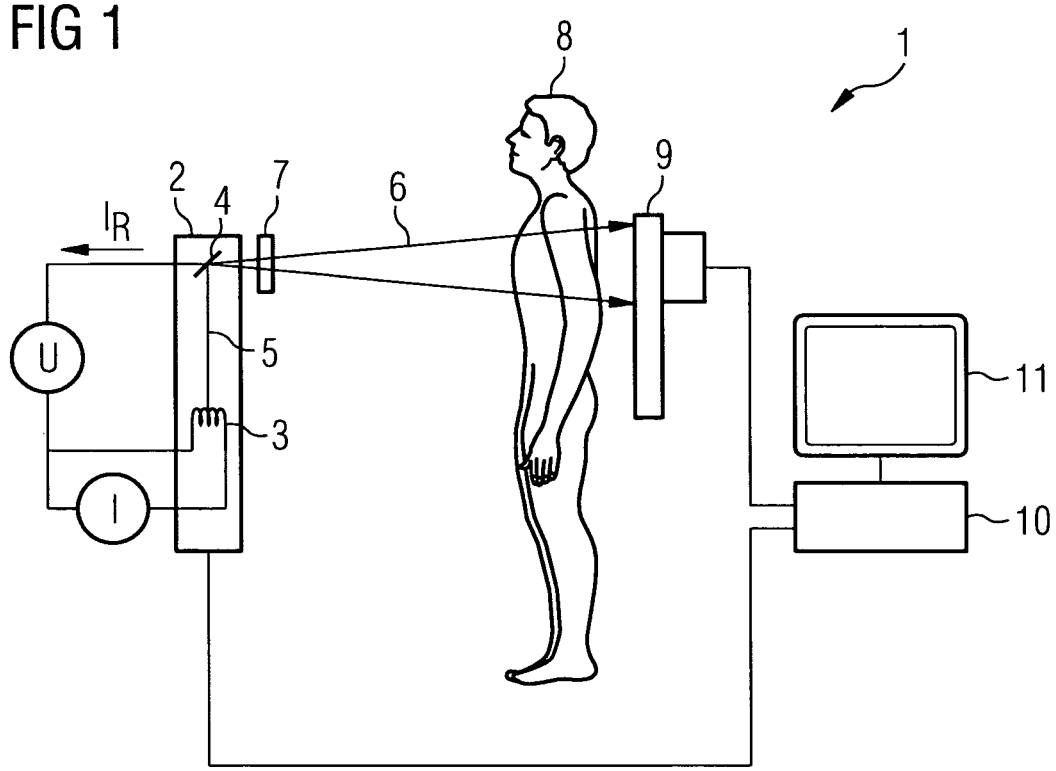
FIG. 1 shows a dual energy X-ray absorptiometry device.

FIG. 1 shows an X-ray machine 1 which can be used to take X-ray pictures for dual energy X-ray absorptiometry. The X-ray machine 1 comprises an X-ray tube 2 having a cathode 3 formed by a filament. The filament 3 can be heated by means of a heating current I, the cathode 3 emitting electrons which are accelerated in the direction of the anode 4 by means of a tube voltage U. This produces an electron beam 5 which is incident on the anode 4 at a focal spot. The electrons decelerated in the anode 4 produce X-ray radiation 6 which first passes through a pre-filter 7 acting as a spectral filter to suppress the low-energy component. The pre-filters 7 are generally thin copper plates which can be mounted in different thicknesses in the beam path of the X-ray radiation 6. The X-ray radiation 6 then penetrates a patient under examination 8.

The X-ray radiation 6 which has passed through the patient 8 is detected by an X-ray detector 9 which registers an attenuation image of the patient 8, the structure of the material attenuating the X-ray radiation 6 in the patient 8 being projected onto the X-ray detector 9. The X-ray recordings containing attenuation images will therefore also be termed projection images.

The X-ray detector 9 is preferably a semiconductor-based flat-panel or large-area detector which has a plurality of detector elements enabling a digital X-ray image to be produced. The detector elements each accommodate one image element and are also termed pixels.

The X-ray detector 9 is followed by a processing unit 10 which generally produces a linear combination of the attenuation images captured at different energy levels of the X-ray radiation 6 by varying the tube voltage U and the pre-filters 7. The composite image generated by linear combination of the attenuation images captured at different energy levels is displayed on a monitor 11.

Linearly combining the attenuation images can involve, for example, taking a difference whereby the bone structure of the patient 8 is eliminated from the composite image. The composite image generated in this way contains the attenuation structure of the soft tissue, which is particularly advantageous for lung examinations.

The attenuation images are acquired at different energy levels by varying in particular the tube voltage U and the pre-filters 7. For example, for the attenuation image in the low-energy range, a lower tube voltage U can be used. In addition, the pre-filters 7 can have a small material thickness so that the low-energy portion of the spectrum produced by the X-ray tube 2 is only slightly suppressed. For the attenuation images in the high-energy range, on the other hand, a high tube voltage U can be used. Moreover, pre-filters 7 with a greater material thickness can be used which preferably allow through the high-energy part of the X-ray spectrum produced by the X-ray tube 2.

Methods will now be described with which the mass densities can largely be precisely determined on the basis of the attenuation images.

As scatter correction is critical for the usability of the composite images, the following description will in particular also include methods whereby the scatter effects can be reduced.

1. Problem

The signal-forming of the X-ray radiation 6 passing through the patient 8 is essentially determined by the emission spectrum $Q_U(E)$, namely the energy spectrum, which is dependent on the applied tube voltage U, by the photons emitted as bremsstrahlung at the anode, and by the transparency $T_F(E)$ of the spectral filters used and by the spectral responsivity $\eta_D(E)$ of the X-ray detector 9.

The resulting normalized rms spectral distributions $W(E; U)$ are defined by:

$$W(E;U)=Q_U(E)T_F(E)\eta_D(E)/c_U$$

where the factor $c_U$ normalizes the integrated normalized rms spectral distribution to the value=1.

Figure 2:
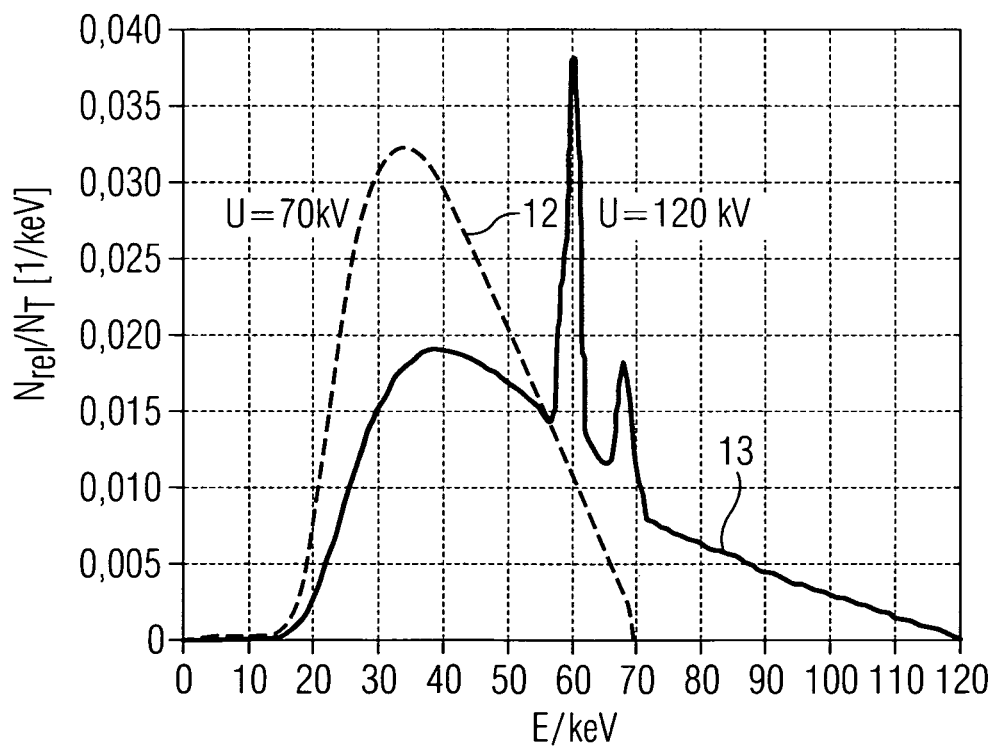
FIG. 2 shows two photon spectra acquired at different tube voltages of an X-ray tube with a tungsten anode.

Examples of two rms spectral distributions corresponding to the tube voltages 60 kV and 120 kV are shown in FIG. 2. In this figure the relative photon frequency $N_{rel}/N_T$ per 1-keV interval is plotted against the photon energy E in keV, where $N_T$ is the total number of photons, an X-ray spectrum 12 being assigned to a tube voltage of 70 kV and an X-ray spectrum 13 to a tube voltage of 120 kV.

Figure 3:
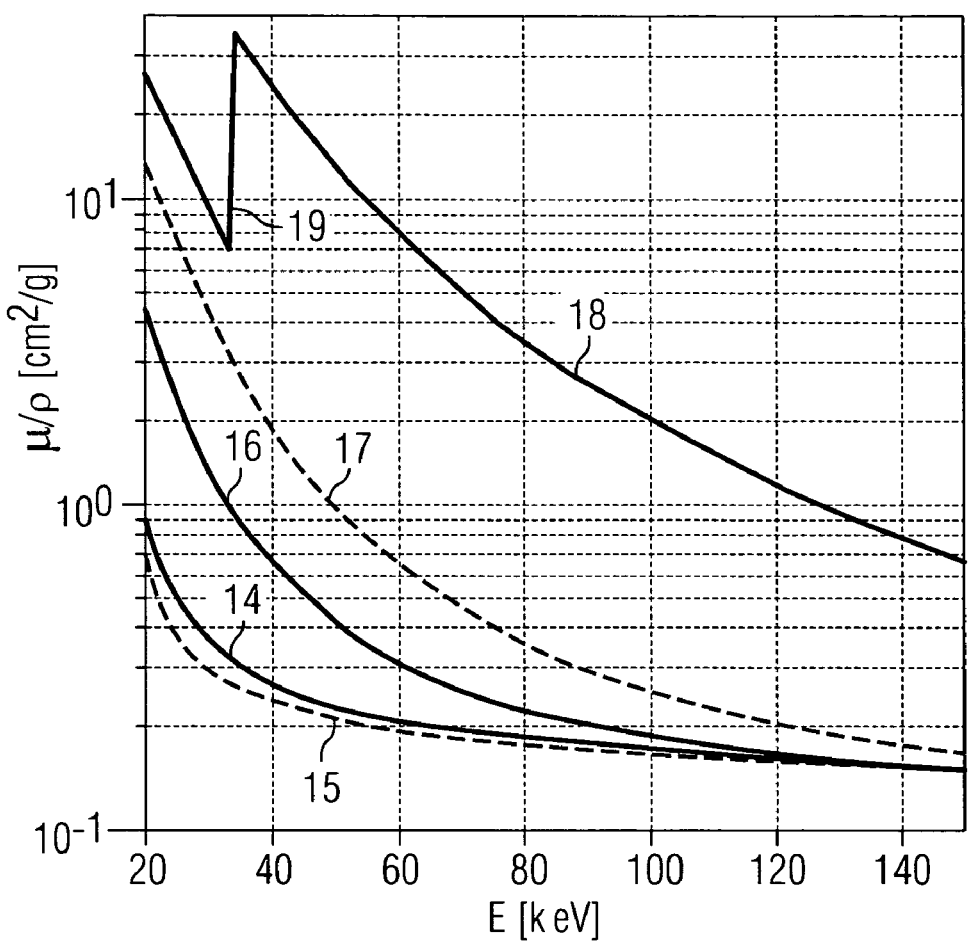
FIG. 3 shows a plot of mass attenuation coefficient versus photon energy for different body parts.

The mass attenuation coefficient for water $(\mu/\rho)(E)$ as a function of photon energy E is shown in FIG. 3, a mass attenuation curve 14 for water being approximately congruent with a mass attenuation curve for blood, although blood has a greater density $\rho$ than water. Fatty tissue, on the other hand, has a mass attenuation curve 15 that is slightly different from the mass attenuation curve 14. Another mass attenuation curve 16 gives the variation of the mass attenuation coefficient of bony tissue. Further mass attenuation curves 17 and 18 describe the variation of the mass attenuation coefficient of calcium and iodine, which has a K-edge 19 at a photon energy of 33.2 keV. Iodine is frequently used as a contrast agent.

As FIG. 3 clearly shows, bony material absorbs X-ray radiation more strongly than soft tissue. However, in the case of bony tissue, the attenuation coefficient of the X-ray radiation falls off more strongly at higher energies than the absorption of soft tissue. Consequently, the primary radiation function does not scale with the energy of the X-ray radiation even when using monochromatic X-ray radiation. Mass density images for bony tissue and soft tissue can be therefore be obtained on the basis of the attenuation images captured at different energy levels. Likewise, because of the differing energy dependence of the mass attenuation curve 14 for water and the mass attenuation curve 15 for fatty tissue, water and fatty tissue can be separated.

Figure 4:
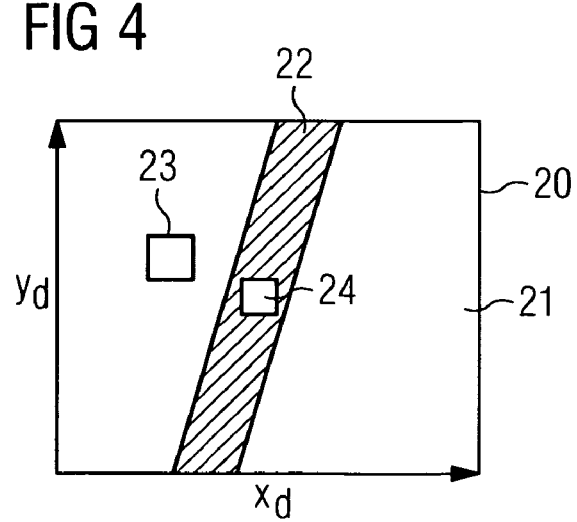
FIG. 4 shows an attenuation image, with an inhomogeneous image area and a homogeneous image area.

FIG. 4 shows an example of an attenuation image 20 with a homogeneous image region 21 and an inhomogeneous image region 22. In the homogeneous image region 21, only tissue with uniform energy versus attenuation coefficient, e.g. soft tissue, is depicted, while in the inhomogeneous image region 22 different kinds of tissue with different energy versus attenuation coefficient, e.g. both soft tissue and bony tissue, are shown. On the basis of an attenuation image which covers both the homogeneous image region 21 and the inhomogeneous image region 22, mass density images for the soft tissue and the bony tissue can be created, it being not absolutely necessary to perform scatter correction across the entire attenuation image. Scatter correction can be carried out, for example, in a correction area 23 located in the homogeneous image region 21 or in a correction area 24 disposed in the inhomogeneous image region 22.

However, in the correction area 24 which is assigned to an inhomogeneous subject region, scatter correction is problematic. For even with the same attenuation of the X-ray radiation, i.e. the same normalized primary intensity $P_1$ or $P_2$, the scattered radiation depends on the material composition in the beam path, i.e. on the mass densities $b_1$ and $b_2$ of the two materials. An example of this is shown in FIG. 5.

Figure 5:
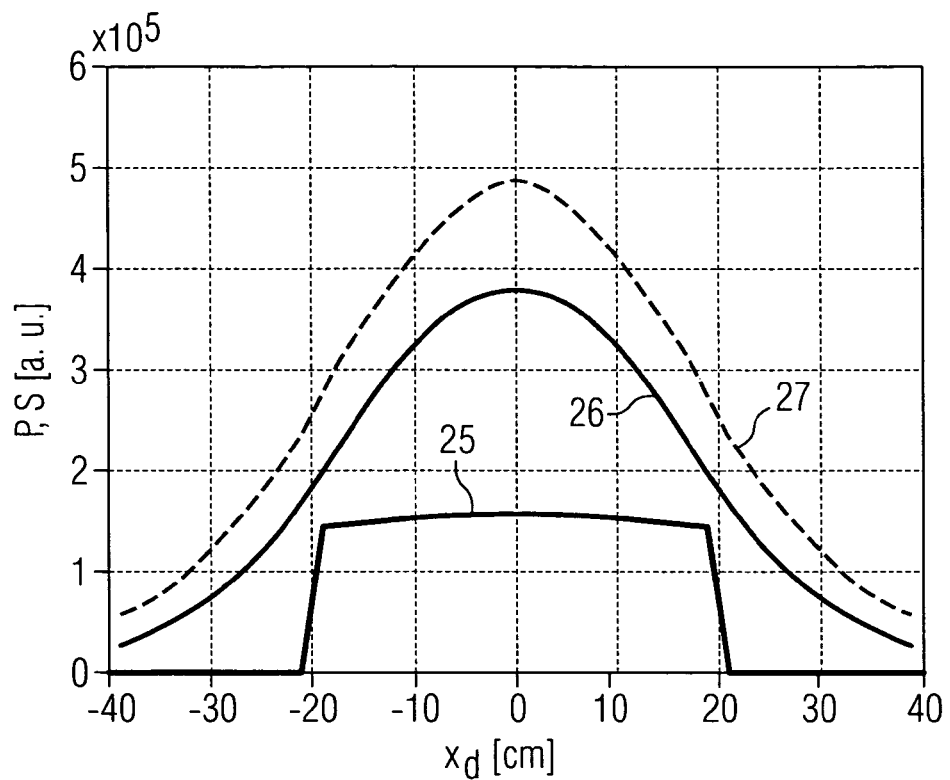
FIG. 5 shows a graph plotting scatter intensity versus different material compositions.

FIG. 5 shows Monte Carlo simulation results which illustrate the dependence of the scatter on the material composition for the same primary radiation. A tube voltage of U=70 kV was adopted. The width of the air gap was set at 20 cm. The surface area of the X-ray detector 9 was set to 40×30 cm². The simulation was performed until the same primary radiation curve 25 was obtained in each case. When the unattenuated radiation first passes through a slice of bony material with a thickness of 5 cm and then water with a thickness of 20 cm, a scatter distribution 26 is produced. If, on the other hand, a non-bony homogeneous water slice 25 cm thick is passed through, the scatter distribution 27 is obtained, both the primary radiation curve 25 and scatter distributions 26 and 27 being plotted in arbitrary units against the coordinates $x_d$ of the detector centerline. The scatter distributions 26 and 27 are each shown to the same scale.

As FIG. 5 clearly shows, the scatter distribution depends on the material composition present. In order to be able to correct the measured projection images in respect of scattered radiation, it is therefore necessary to know the mass density of the individual materials.

Two measured values for the same examination subject will now be considered, acquired using two different tube voltages $U_1$ and $U_2$, in some cases also different filters at the tube or detector end. We denote the rms spectral distributions by:

$$W_1(E)=W(E;U_1), W_2(E)=W(E;U_2)$$

It is assumed that all the usual calibrations for digital X-ray detectors 9 have been carried out, specifically dark image subtraction and correction of the different pixel sensitivities. It is also assumed that correct $I_0$ normalization has been performed, $I_0$ normalization being understood as follows: the full unattenuated intensity without attenuating object is determined for the two spectra and each measured intensity value at each pixel of the X-ray detector 9 is normalized by means of division by the corresponding $I_0$ value. The following description always relates to normalized intensity values, whether it now be primary radiation, scattered radiation or measured total radiation intensity values, the latter consisting of the sum of primary radiation and scattered radiation.

In the following description, the following designations apply:

$I_1$, $I_2$ normalized measured total intensities for spectrum $W_1(E)$ or $W_2(E)$,
$P_1$, $P_2$ normalized, initially unknown primary intensities,
$S_1$, $S_2$ normalized, initially unknown scatter intensities.

For the normalized primary intensities (=primary attenuations) for the spectra $W_1(E)$ and $W_2(E)$ in the case of homogeneous tissue if the relevant X-ray measurement beam traverses the same rms path length X [cm] or mass density X [g/cm$^2$], theoretically:

$$P_1 = F_1(X) = \int_0^{eU_1} e^{-\mu(E)X} W_1(E) dE$$

$$P_2 = F_2(X) = \int_0^{eU_2} e^{-\mu(E)X} W_1(E) dE$$

Note that in these equations, $\mu$ in the exponent is to be understood as the mass attenuation coefficient if X is interpreted as the mass density. If, on the other hand, X is taken to be the path length, $\mu$ is to be understood as the linear attenuation coefficient.

In the context of dual energy X-ray absorptiometry, the qualitative separation of two materials is usually performed according to the following empirical formula:

$\tilde{b}_1 = -\log(I_1) + w_1 \log(I_2)$ $\tilde{b}_2 = \log(I_1) - w_2 \log(I_2)$ Here the variables on the left-hand side are grayscale images, the empirical factors $w_1$, $w_2$ having to be selected such that visually a maximally good separation of the two materials is achieved. $I_1$ and $I_2$ on the right-hand side are the measured intensities in the higher- and lower-energy intensity image. In general, $I_1$ and $I_2$ contain different fractions of the scattered radiation. This means that the selection of the empirical factors $w_1$, $w_2$ is also dependent on the different scatter fractions. The grayscale images on the left-hand side initially represent no physical variables. The grayscale images obtained by linear combination can only be interpreted approximately, by means of suitable scaling factors and additive constants, as pseudo material thicknesses of the two materials to be selected, e.g. as material thicknesses of soft tissue and bone.

A method will therefore be described below with which, from the attenuation images, separated mass density images can be produced with a high degree of accuracy in respect of the individual components, with scatter effects being eliminated.

2. General Scatter Correction Procedures in Inhomogeneous Image Regions

In the methods detailed below, the following three procedures are described in general terms:

2.1 Inversion

With a first procedure, from given pairs of normalized primary intensity values $P_1$ and $P_2$ for the two spectra, the corresponding mass densities $b_1$ and $b_2$ of the two materials to be separated, e.g. soft tissue and bone, are calculated. Normalization is performed by dividing the measured intensity values $I_1$ and $I_2$ by the corresponding unattenuated intensity values $I_{1,0}$ and $I_{2,0}$. We denote this procedure by:

$$M^{-1}(\underline{P}) = \underline{b} \quad (\#1)$$

where the vectors signify $\underline{P}=(P_1,P_2)$, $\underline{b}=(b_1,b_2)$. This procedure is a point operation which can be performed individually for each pixel (x, y) of the X-ray detector 9. The physical background will be explained in greater detail below in conjunction with the explanation of the exemplary embodiments.

2.2 Scatter Estimation

In addition, a second procedure is carried out with which scatter intensity distributions $S_1(x, y)$ and $S_2(x, y)$ for the two spectra can be calculated from predefined spatial primary intensity distributions $P_1(x, y)$ and $P_2(x, y)$ for both spectra and/or predefined spatial mass density distributions $b_1(x, y)$ and $b_2(x, y)$ of the two materials to be separated. We denote this procedure by $$S_{estim}(\underline{P};\underline{b}) = \underline{S} \quad (\#2)$$

where the vectors signify $\underline{P}=(P_1,P_2)$, $\underline{b}=(b_1,b_2)$, $\underline{S}=(S_1,S_2)$ and are functions of (x, y) in each case. The semicolon between the variables on the left-hand side are meant to indicate that in some cases the explicit dependency can be omitted from either variable. The subscript "estim" is to indicate that these are mathematical models with which the scattered radiation is to be estimated.

For the second procedure, an expansion of a convolution model of the type outlined in ZELLERHOFF, M.; SCHOLZ, B.; RÜHRNSCHOPF, E.-P.; BRUNNER, T.: Low contrast 3D reconstruction from C-arm data. In: Proceedings of SPIE. Medical Imaging, 2005, Vol. 5745, pages 646 to 655 is a possible option. Such a convolution model can be implemented as a relatively fast algorithm. Monte Carlo simulations, which are time-consuming even using today's standard computers, are also possible. Both alternatives will be explained in greater detail in Sections 4.1 and 4.2 in conjunction with concrete examples.

2.3 Scatter Correction

As a third procedure, a scatter correction algorithm is executed with [which the] predefined intensity distributions $\tilde{P}_1(x,y), \tilde{P}_2(x,y)$ which are superimpositions of primary and scattered radiation are corrected using given scatter intensity distributions $S_1(x, y)$ and $S_2(x, y)$ such that primary intensity distributions $P_1(x, y)$ and $P_2(x, y)$ are obtained—at least approximately—therefrom. Such a correction procedure is denoted as $$S_{korr}(\underline{\tilde{P}};\underline{S}) = \underline{P} \quad (\#3)$$

The most important correction algorithms are explained in Section 4.3.

3. Iteration Methods

The equations (#1), (#2) and (#3) can be solved iteratively. Iteration algorithms generally consist of three parts: an iteration start with predefined initial values, an iteration rule by means of which the initial values are modified, and a termination condition.

Using the three procedures described, the following iteration method, applied to two components, can now be carried out in the context of dual energy X-ray absorptiometry:

3.1 Iteration Start

Initially only the measured intensity distributions $I_1(x, y)$ and $I_2(x, y)$ for the two spectra and the associated intensities for unattenuated radiation $I_{1,0}$ and $I_{2,0}$ are taken as given. As we still know nothing about the scatter, we set the uncorrected normalized intensity distributions as starting values:

$$\underline{P}^{(0)} = \begin{bmatrix} I_1/I_{1,0} \\ I_2/I_{2,0} \end{bmatrix} \tag{\#4a}$$

$$\underline{b}^{(0)} = M^{-1}(\underline{P}^{(0)}) \tag{\#4b}$$

As $P^{(0)}$ has not yet been scatter-corrected, it may happen that one of the two material densities comes out negative. This must then be set=0. For soft part/bone separation it will generally be the bone component which is initially assigned negative values.

3.2 Iteration Rule

The iteration rule determines the transition from the iteration with the subscript n (n≧0) to the next iteration with the subscript n+1. In the following we shall omit the pixel coordinates (x, y). Note that we are dealing with two-dimensional functions.

$$\underline{S}^{(n)} = S_{estim}(\underline{P}^{(n)}, \underline{B}^{(n)}) \tag{\#5a}$$

$$\underline{P}^{(n+1)} = S_{korr}(\underline{P}^{(n)}, \underline{S}^{(n)}) \tag{\#5b}$$

$$\underline{b}^{(n+1)} = M^{-1}(\underline{P}^{(n+1)}) \tag{\#5c}$$

Again it can happen that one of the two material densities comes out negative. This must then be set=0.

3.3 Iteration Termination

The iteration sequence can be terminated when the change between consecutive iterations is less than a specifiably small threshold. In most cases, especially for a relatively small to moderate scatter fraction (S<=P), one to three iterations are generally sufficient. The maximum number of iterations to be carried out can be fixed or dependent on the S/P ratio.

4. Details of the Operations to be Performed

In Section 2 the essential mathematical operators were listed, but only described in a generally formal manner rather than concretely. Here the individual operations and variants thereof will be described.

4.1 $M^{-1}$: Calculation of Material Densities from Dual Energy Projection Data For the normalized primary intensities for the spectra $W_1(E)$ and $W_2(E)$ in the case of two radiologically different materials with mass attenuation coefficients $\alpha_1(E) = (\mu_1/\rho_1)(E)$ and $\alpha_2(E) = (\mu_2/\rho_2)(E)$ as a function of the mass densities $b_1$ and $b_2$ [g/cm$^2$] which the X-ray beam penetrates, the following equations basically apply $$M_1(b_1, b_2) = \int_0^{eU_1} e^{-\alpha_1(E)b_1 - \alpha_2(E)b_2} W_1(E) dE \tag{\#6a}$$

$$M_2(b_1, b_2) = \int_0^{eU_2} e^{-\alpha_1(E)b_1 - \alpha_2(E)b_2} W_2(E) dE \tag{\#6b}$$

This can also be written in the form of a vector function as:

$$M(\underline{b}) = \begin{bmatrix} M_1(b_1, b_2) \\ M_2(b_1, b_2) \end{bmatrix} \tag{\#7}$$

The rms spectra $W_1(E)$ and $W_2(E)$ can be taken as known, said rms spectra $W_1(E)$ and $W_2(E)$ comprising the emission spectrum of the X-ray tube 2, the effect of the spectral filters and the energy-dependent detector responsivity. FIG. 2 shows two typical spectra 12 and 13 and FIG. 3 the energy-dependent mass attenuation coefficient.

The functions $M_1(\underline{b})$, $M_2(\underline{b})$ describing the primary intensities can basically be precalculated as functions of the mass thicknesses $b=(b_1,b_2)$ or also determined experimentally. As they partially fall strictly monotonically relative to the two variables $b_1$ and $b_2$, at least in the energy ranges and materials that are of interest in medical diagnostics, the vector operators M can be inverted. Inversion can be performed by means of standard numerical analysis methods, such as the Newton-Raphson method for vector functions. Such methods are described, for example, in PRESS, FLANNERY, TEUKOLSKY, VETTERLING: Numerical Recipes. The Art of Scientific Programming, Cambridge University Press, 1989, pages 268 to 273.

Note that, for inversion purposes, it is advantageous to logarithmize the equation (#6a,b) on the right-hand side.

Note also that at the start of the iterations, the case may also arise that inversion can only be accomplished with one (or both) of the thicknesses outside the physical definition range, as the corrected estimates of the primary intensities $P_1$ and $P_2$ are still erroneous because of the still imprecise scatter correction. If the inverse $M^{-1}$ is to be calculated throughout the occurring value range of the normalized measured values $P_1$ and $P_2$, the vector function must be calculated accordingly as per equation (#7) across the physical definition range of $b_1$ and $b_2$—particularly also for notional negative thicknesses.

4.2 $S_{estim}$: Estimation Models for Scatter Distributions

A generalization of the already mentioned convolution model or a Monte Carlo method, for example, can be used for determining the scatter distribution.

In both methods, the information contained in the measured total intensities can be used to determine the scattered radiation and the mass density of the two material components, mostly water and bone.

4.2.1 Scatter Determination with Generalized Convolution Model

For the convolution model according to ZELLERHOFF, M.; SCHOLZ, B.; RÜHRNSCHOPF, E.-P.; BRUNNER, T.: Low contrast 3D reconstruction from C-arm data. In: Proceedings of SPIE. Medical Imaging, 2005, Vol. 5745, pages 646 to 655, the scatter distribution is estimated using the following setup:

$$S(x,y) = [pe^{-p}C(p)]**G(x,y) \tag{\#8}$$

where $p(x, y) = -\ln(P(x, y))$ and $P(x, y)$ is an estimate of the normalized primary distribution.

$G(x, y)$ is a two-dimensional convolution core which empirically describes the low-pass filtering (smearing) caused by scatter propagation.

$C(p)$ is a calibrating weight function:

$$C(p) = C(b_0(p); U, F_{yz}, a, \ldots) \tag{\#9a}$$

This weight function describes the scatter-to-primary ratio S/P for standard bodies, e.g. for homogeneous plates or elliptical cylinders, as a function of the layer thickness $b_0(p)$ of water equivalent material. This layer thickness can be unambiguously determined from the logarithmized primary attenuation $p=-\ln(P)$ on the basis of the known beam hardening correction.

C also depends on the physical acquisition parameters: voltage U, radiation filter, collimated field size $F_{yz}$ of the detector, scatter grid, air gap and similar parameters.

C can be calculated in advance by means of Monte Carlo methods and stored in a table. In the case of fixed acquisition parameters, C is only dependent on one variable, namely the water equivalent layer thickness $b_0(p)$. As two recordings are made using two different energy spectra at different tube voltages, two tables $C_1$ and $C_2$ are required.

Figure 6:
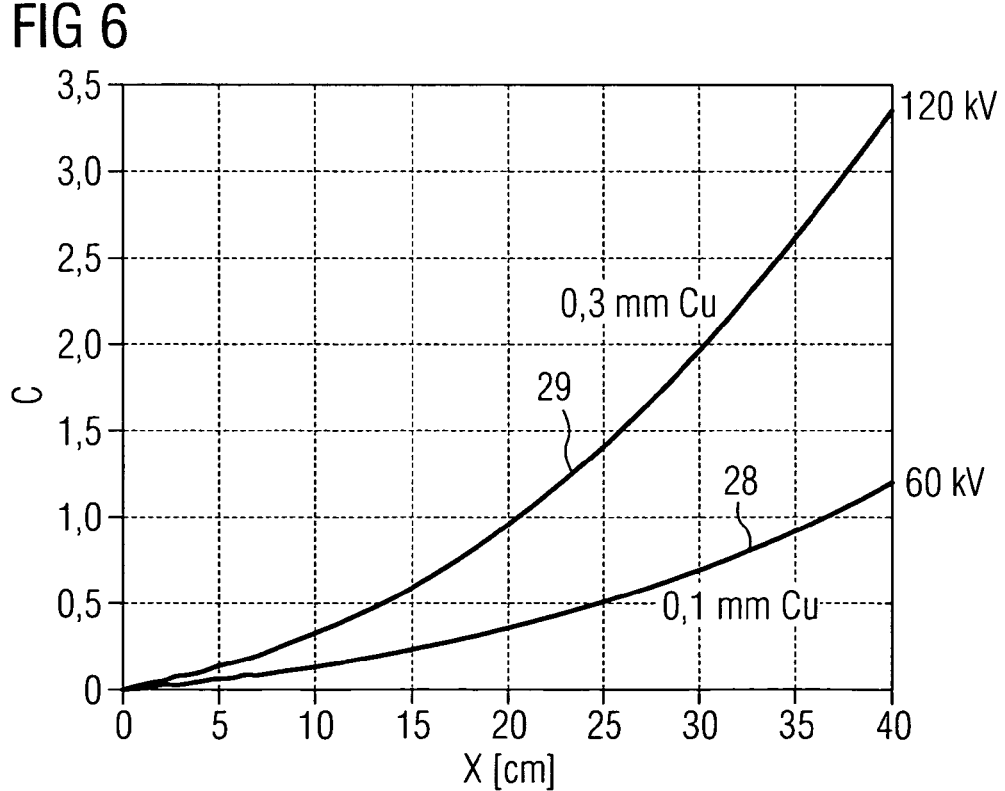
FIG. 6 shows a graph plotting scatter-to-primary ratio versus water thickness for different tube voltages.

Two typical tables are graphically illustrated in FIG. 6.

In FIG. 6 a ratio curve 28 gives the ratio $C_1$ of the scatter to primary intensity for a tube voltage U=60 kV and a pre-filter 7 with 0.1 mm copper, and a ratio curve 29 gives $C_2$ corresponding to a tube voltage U=120 kV and a pre-filter 7 with 0.3 mm copper.

Using the weight function in equation (#9a), we obtain a simplified scatter correction within the iteration loop in the equations (#5a-c), a water equivalent path length derived from the estimated primary radiations $P_1$ and $P_2$ and from it in turn a scatter fraction S/P via table C being used and iteratively improved.

The here described generalization of the known approach consists in that the tables $C_1$ and $C_2$ for the two spectra, corresponding to different voltages $U_1$ and $U_2$ and in some cases different pre-filtering, depend not just on one variable, namely the water layer thickness, but are created as a function of two variables $b_1$ and $b_2$, the water and bone thickness:

$$C_1 = C(b_1, b_2; U_1, F_{yz}, a, \ldots) \quad (\#9b)$$

$$C_2 = C(b_1, b_2; U_2, F_{yz}, a, \ldots) \quad (\#9c)$$

New current values of the two material thicknesses $b_1$ and $b_2$ are produced at each iteration step. The new values for the material thicknesses $b_1$ and $b_2$ must then be used as new input values to the tables $C_1$ and $C_2$, which are now dependent on the two parameters $b_1$ and $b_2$, in order to obtain an iteratively improved scatter estimate.

An explicit dependence on p or P is no longer apparent. This is replaced by the dependence on $b_1$ and $b_2$.

4.2.2 Scatter Estimation with Monte Carlo Method

It is basically also conceivable to calculate directly via Monte Carlo methods the scatter distribution for the two material thickness distributions $b_1(x, y)$ and $b_2(x, y)$ currently re-estimated at each iteration step. However, Monte Carlo simulation is very compute intensive, so that using the Monte Carlo method requires a large amount of computing power.

4.3 $S_{korr}$ Scatter Correction Algorithms

Scatter correction can be performed both subtractively and multiplicatively, two spectra being corrected in each case.

Subtractive scatter correction is particularly simple and consists in subtracting the estimated scatter intensities from the relevant uncorrected normalized intensity distributions:

$$P_1^{(n+1)}(x,y) = I'_1(x,y) - S_1^{(n)}(x,y)$$

$$P_2^{(n+1)}(x,y) = I'_2(x,y) - S_2^{(n)}(x,y) \quad (\#10a)$$

(x, y) denote pixel coordinates on the detector and, for the intensities $I_1(x,y)$ and $I_2(x,y)$, we write $I'_1(x, y) = I_1(x, y)/I_{1,0}$ and $I'_2(x, y) = I_2(x, y)/I_{2,0}$.

As a constant value is only a very coarse approximation, it may happen that, in equation (#5), subtraction yields negative values. Such physically nonsensical values should be prevented where possible. One countermeasure is to use multiplicative scatter correction instead of subtractive correction in (#10a):

$$P_1^{(n+1)}(x, y) = P_1^{(n)}(x, y) \frac{I'_1(x, y)}{P_1^{(n)}(x, y) + S_1^{(n)}(x, y)} \quad (\#10b)$$

$$P_2^{(n+1)}(x, y) = P_2^{(n)}(x, y) \frac{I'_2(x, y)}{P_2^{(n)}(x, y) + S_2^{(n)}(x, y)}$$

For the case $S_1^{(n)}(x,y) \ll I_1(x,y)$ and $S_2^{(n)}(x,y) \ll I_2(x,y)$, multiplicative correction as per equations (#10b) transposes into subtractive correction in accordance with equations (#10a).

5. Location Dependence

The spatial distribution of scattered radiation, apart from noise, is generally smooth and therefore low-frequency. This means that it is sufficient to determine the scatter pointwise or in regions of interest at very few places on the detector surface. The simplest approximation is therefore a suitable constant average for the secondary radiation intensity.

For all-inclusive estimation of the average background scatter intensity it suffices, as shown FIG. 4, to select a suitable correction area 23 or 24 of interest and to take an average over said area for the lower- and higher-energy projection image. For this value pair $\bar{I}_1, \bar{I}_2$ the corresponding value pair $\bar{S}_1, \bar{S}_2$ of the scatter intensities is determined by iteration. The overlines used here are to indicate that these are estimated, averaged or even constant values.

Scatter correction outside the correction area 23 or 24 then consists in subtracting the estimated scatter intensities from the relevant uncorrected normalized intensity distributions:

$$\tilde{P}_1(x,y) = I_1(x,y) - \bar{S}_1$$

$$\tilde{P}_2(x,y) = I_2(x,y) - \bar{S}_2 \quad (\#11)$$

On the left-hand side are the corrected primary distributions, while $\bar{S}_1$ and $\bar{S}_2$ are the scatter intensities obtained after iteration. (x, y) denote pixel coordinates on the detector. The tilde serves to indicate that this is uncorrected data, i.e. estimates based on a correction.

As a constant value is only a very coarse approximation, it may happen that, in equation (#11), subtraction yields negative values. Such physically nonsensical values should be prevented where possible. One course of action is to select a suitable correction area 23 or 24 in the region of strong attenuation for all-inclusive scatter determination. A region with heavy attenuation is a region with low $I_{1,2}$ values.

Another course of action is to perform multiplicative scatter correction instead of subtractive correction in equation (#11):

$$\tilde{P}_1(x, y) = J_1(x, y) = \frac{1}{1 + \frac{\bar{S}_1}{J_1(x, y)}} \quad (\#12)$$

$$\tilde{P}_2(x, y) = J_2(x, y) \frac{1}{1 + \frac{\bar{S}_2}{J_2(x, y)}}$$

For the case $\bar{S}_1 \ll J_1(x,y)$ and $\bar{S}_2 \ll J_2(x,y)$, equations (#12) transpose into (#11).

The location dependency of the scatter background can also be handled by applying the correction method described above in conjunction with an individual pixel to a uniformly coarse grid of regions of interest or sampling points on the detector and expanding the result by means of interpolation from the coarse grid to the original fine pixel grid. The corrections in accordance with equations (#10) and (#11) must then be extended correspondingly: $\overline{S}_1$, $\overline{S}_2$ are then no longer constants, but functions dependent on the pixel coordinates (x, y) even if in general this dependence is only weak.

The location dependence can also be obtained by applying the method described for an individual pixel or region of interest to a uniform coarse grid of regions of interest or sampling points on the detector. Interpolation onto the original fine grid can then be performed by convolving the scatter fraction values determined on the coarse grid with a wide distribution function.

The fact that the scatter is spatially very low-frequency, is also taken into account by conventional correction methods by means of smoothing convolution operations. Corresponding methods are described in ZELLERHOFF, M.; SCHOLZ, B.; RÜHRNSCHOPF, E.-P.; BRUNNER, T.: Low contrast 3D reconstruction from C-arm data. In: Proceedings of SPE. Medical Imaging, 2005, Vol. 5745, pages 646 to 655. Combining the approach described here with more complex convolution models of this kind is basically possible. For example, the scatter fraction can be determined by one of the methods described here in parallel with a conventional method and the results then averaged.

6. Method Sequence

The scatter correction methods described here are in each case prereconstructive methods which determine the scatter fraction on the basis of the attenuation images, without using at least approximately determined three-dimensional volume images of the examination subject. It these methods it is rather the additional information provided by attenuation images captured at differing energy levels that is used to estimate the scatter fraction.

Figure 7:
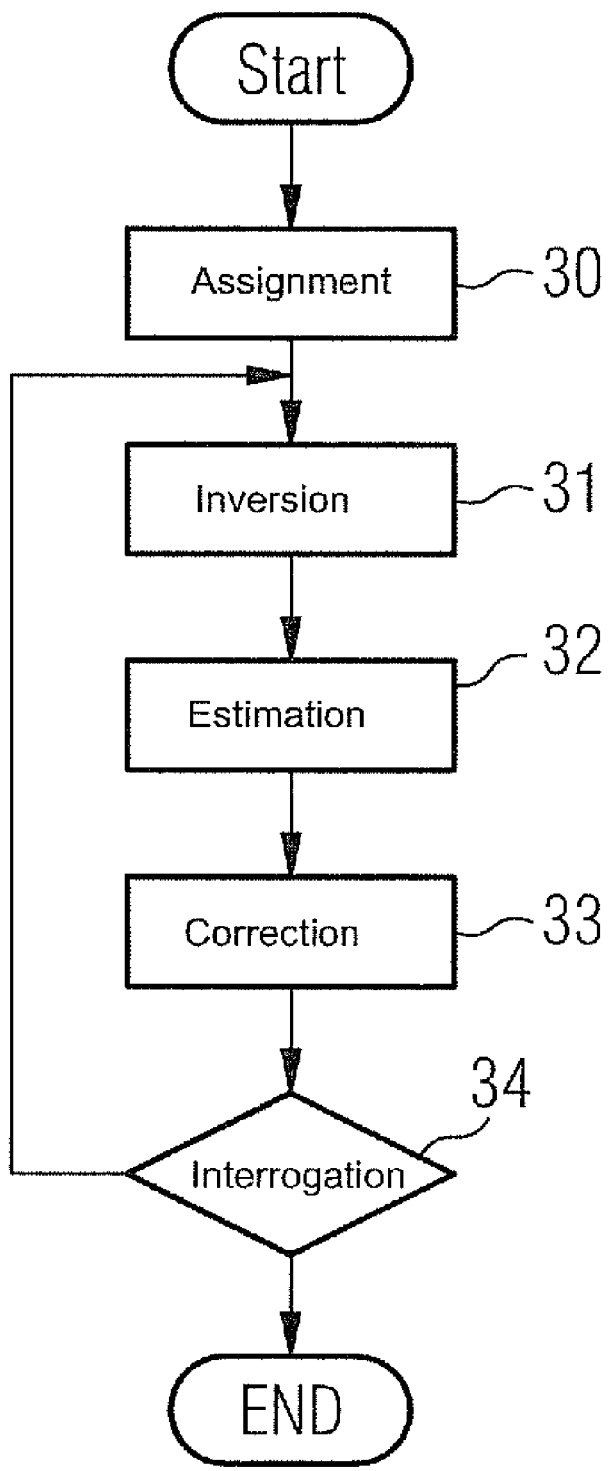
FIG. 7 shows a flowchart of the scatter correction method.

FIG. 7 shows a flowchart of the method.

This method begins with value assignment 30 followed by inversion 31 in accordance with equation (#1), variables characteristic of a multi-dimensional mass density being produced, on the basis of which estimation 32 in accordance with equation (#2) can be performed. This is followed by correction 33 of the starting values for the primary attenuation fractions in accordance with equation (#3). By means of interrogation 34 it can finally be decided whether inversion 31 using the corrected primary attenuation fractions is repeated.

7. Simplified Method

In addition to the previously described methods, it is also possible to perform separate scatter correction for the individual attenuation images and then perform inversion in accordance with equation (#1) on the basis of the primary radiation intensities obtained. For example, for the low-energy attenuation image and the high-energy attenuation image a spatially low-frequency scatter distribution can be determined in each case and subtracted from the attenuation values of the low-energy or high energy attenuation images.

The secondary radiation fractions can be determined in a measurement-based manner by means of the beam-stop method or a computational method. The disadvantage of the beam-stop method is that it requires two additional measurements. However, because of the (apart from noise) low-frequency nature of the scatter distribution, these measurements can be taken with very low dose and only minimal additional radiation load. If the secondary radiation fractions are obtained using one of the known computational methods, no additional measurements need be performed on the patient. The known scatter correction measurements can also be performed in real-time, but in some circumstances require access to a database which must be created in advance by measurements or Monte Carlo simulation as part of system development.

The subsequent inversion of equation (#1) cannot generally be performed analytically. On the other hand, numerical inversion using the mentioned Newton-Raphson is usually possible. Inversion can also be carried out in advance and stored in tabular form so that, in the specific application, the solving of the equation (#1) can be replaced by looking it up in a solution table.

8. Demonstration Examples

An example from medical imaging which illustrates the reconstruction of mass density images from attenuation images will now be described on the basis of FIGS. 8 to 13.

A typical application for dual energy X-ray absorptiometry is separating between soft tissue and bony tissue in a thorax or lung x-ray in order to be able to detect lung nodules.

Figure 8:
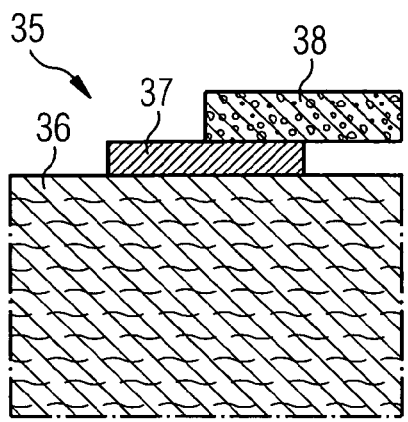
FIG. 8 shows a cross section through a virtual phantom to illustrate the reconstruction of mass density images.
Figure 9:
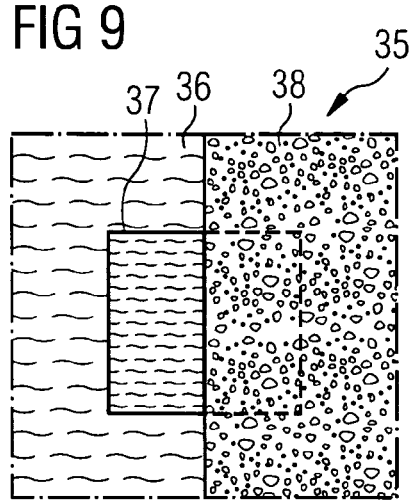
FIG. 9 shows a plan view of the virtual phantom from FIG. 8.

The method is tested using a phantom 35. FIG. 8 shows a cross section through the phantom 35, while FIG. 9 shows a plan view of the phantom 35.

The phantom 35 comprises cuboidal soft tissue 36 on which cuboidal tumor tissue 37 likewise consisting of soft tissue is centrally disposed. Bony tissue 38 now extends over half of the soft tissue 36, said bony tissue also half-covering the tumor tissue 37.

Figure 10:
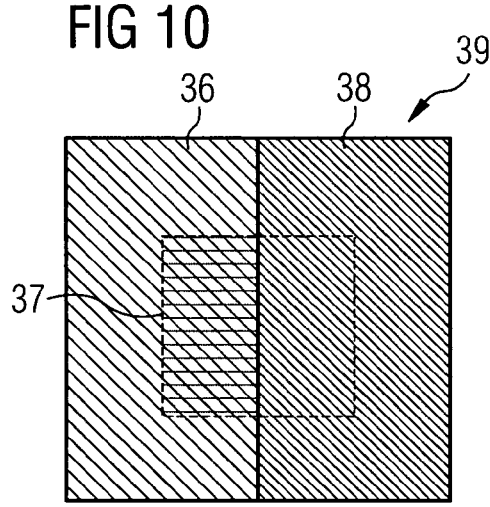
FIG. 10 shows a simulation of a low-energy X-ray recording of the phantom from FIGS. 8 and 9.
Figure 11:
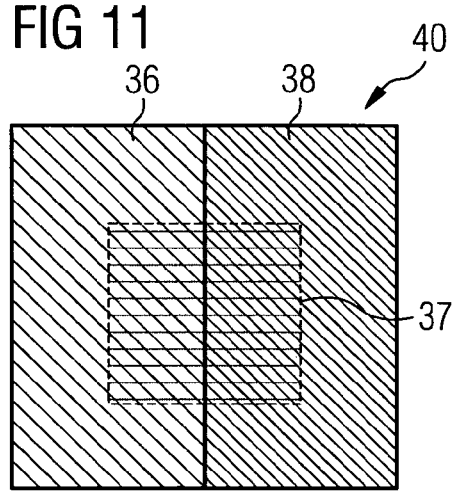
FIG. 11 shows a simulation of a high-energy X-ray recording of the phantom from FIGS. 8 and 9.

FIG. 10 now shows an X-ray shot 39 taken at a low energy level. For the low energy X-ray shot 39, a recording with U=60 kV and 0.1 mm copper pre-filtering was simulated by a Monte Carlo method. FIG. 11, on the other hand, show an X-ray shot 40 that has been taken at a high energy level. In particular a tube voltage of U=120 kV and a copper pre-filter 0.3 mm thick was simulated. For the sake of clarity, in the X-ray shots 39 and 40 the different grayscale values have been indicated by hatching of different density, the hatching density being greater the darker the corresponding image region.

Figure 12:
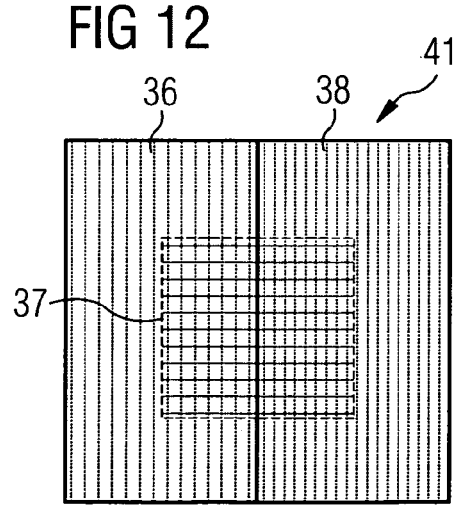
FIG. 12 shows a soft tissue image of the virtual phantom from FIGS. 8 and 9, reconstructed on the basis of the X-ray images from FIGS. 9 and 10.
Figure 13:
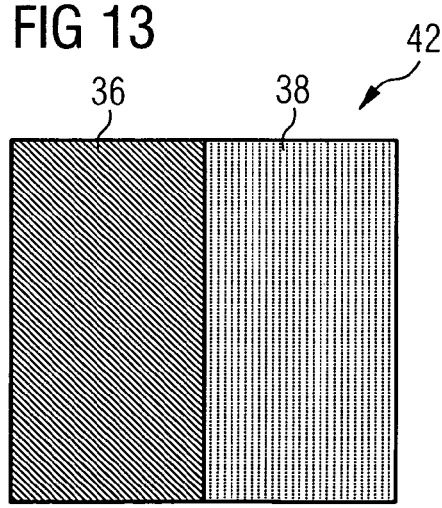
FIG. 13 shows a bone image of the virtual phantom from FIGS. 8 and 9, reconstructed on the basis of the X-ray images from FIGS. 9 and 10.

While the attenuation images obtained are illustrated in FIGS. 10 and 11, FIGS. 12 and 13 show mass density images which have been created using the simplified method described in the previous Section 8. In particular, FIG. 12 shows a soft tissue image 41 and FIG. 13 a bone image 42. Also for the soft tissue image 41 and the bone image 42, the grayscale value is represented by the density of the hatching, it being the case for the soft tissue image 41 and the bone image 42 that the more material in the beam path, the lighter the soft tissue image 41 or the bone image 42. From the soft tissue image 41 it is clearly discernible that in the region of the tumor tissue 37 the lightness is essentially constant, irrespective of whether or not the image half has been covered by bony tissue 38. However, the region of the bony tissue 38 also remains detectable in the soft tissue image 41 on the basis of the stronger image noise. This is also attributable in particular to the poor signal-to-noise ratio in the region of the bony tissue 38, as the X-ray radiation is more heavily absorbed there. A remedy for this is noise-adaptive image filtering which provides stronger local smoothing in higher-noise regions.

9. Advantages

Material separation accuracy can be significantly increased by means of the iteration cycle which includes scatter correction.

In addition, iterative integration enables scatter correction to be improved by refining the scatter estimation model with the additional information about the mass thicknesses of two material components—which would not be available without iteration. In particular, scatter [correction] can be carried out even when soft tissue and bone are present.

Because of the underlying physical-mathematical model which is described using formal variables or parameters, the calculation process can easily be systematically adapted to changed conditions by varying the parameters or parameter functions. For example, a change in the spectra can be effected by selecting other voltages, by modifying the radiation filters or by varying the acquisition geometry.

Basically, the method described here opens up the possibility of optimizing the parameters of multispectrum imaging in terms of suitable evaluation quantities for specifying the materials to be separated. In particular, the voltage used, the type of filters, and the detector dose can be used to improve the signal-to-noise ratio in proportion to the patient dose.

The invention claimed is:

1. A method for creating a mass density image of an examination subject, comprising:
   generating radiation using a radiation source;
   X-raying the examination subject by the radiation;
   capturing attenuation images at a plurality of different energy levels by detecting the radiation;
   determining mass density values for a multi-dimensional mass density in the examination subject by inverting a multi-dimensional attenuation function by which the multi-dimensional mass density in the examination subject is a function of attenuation values of the attenuation images; and
   creating the mass density image from the attenuation images based on the determined mass density values,
   wherein a secondary radiation fraction caused by scatter is determined and the attenuation images are corrected in respect of the secondary radiation fraction to a primary attenuation fraction produced by attenuation, and
   wherein the secondary radiation fraction is determined in a correction image area that yields a same mass density when calculates the inverse attenuation function.

2. The method as claimed in claim 1, wherein the secondary radiation fraction is dependent on the multi-dimensional mass density.

3. The method as claimed in claim 1, wherein the secondary radiation fraction is determined by convoluting the primary attenuation fraction with a distribution function that is dependent on the multi-dimensional mass density.

4. The method as claimed in claim 3, wherein the distribution function is determined in advance by Monte Carlo simulation.

5. The method as claimed in claim 1, wherein the secondary radiation fraction is determined by Monte Carlo simulation of a scatter at the examination subject considering the multi-dimensional mass density.

6. The method as claimed in claim 1, wherein the primary attenuation fraction is corrected based on the secondary radiation fraction after the determination of the multi-dimensional mass density.

7. The method as claimed in claim 6, wherein the multi-dimensional mass density is re-determined based on the corrected primary attenuation fraction.

8. The method as claimed in claim 1, wherein the correction image area represents a region of the subject that is inhomogeneous in respect of an attenuation coefficient.

9. The method as claimed in claim 8, wherein the attenuation function is dependent on the multi-dimensional mass density.

10. The method as claimed in claim 8, wherein the correction image area with the inhomogeneous attenuation coefficient represents a body region of the subject comprising a bone or an implant that is not made from hydrocarbon-based plastics.

11. The method as claimed in claim 1, wherein the correction image area comprises a single pixel of the attenuation images.

12. The method as claimed in claim 1, wherein image values of the attenuation images in the correction image area are averaged and the secondary radiation fraction is determined based on the averaged image values.

13. The method as claimed in claim 1, wherein a secondary radiation intensity is determined from the secondary radiation fraction in the correction image area and subtracted from image values outside the correction image area.

14. The method as claimed in claim 1, wherein a secondary radiation intensity is determined from the secondary radiation fraction in the correction image area and used to generate a correction factor for correcting image values outside the correction image area.

15. The method as claimed in claim 1, wherein the secondary radiation fraction is determined in an area comprising the correction image area of a grid extending over the attenuation images.

16. The method as claimed in claim 1, wherein image values outside the correction image area are corrected as a function of the secondary radiation fraction in an area adjacent the correction image area.

17. The method as claimed in claim 1, wherein the multi-dimensional attenuation function is iterately inverted until a change between consecutive iterations is less than a specific small threshold.

18. A device for creating a mass density image of an examination subject, comprising:
    a radiation source that generates radiation;
    a detector device that captures attenuation images at a plurality of different energy levels by detecting the radiation passing through the examination subject; and
    a processing unit that:
       determines mass density values for a multi-dimensional mass density in the examination subject by inverting a multi-dimensional attenuation function by which the multi-dimensional mass density in the examination subject is a function of attenuation values of the attenuation images, and
       creates the mass density image from the attenuation images based on the determined mass density values,
    wherein a secondary radiation fraction caused by scatter is determined and the attenuation images are corrected in respect of the secondary radiation fraction to a primary attenuation fraction produced by attenuation, and
    wherein the secondary radiation fraction is determined in a correction image area that yields a same mass density when calculates the inverse attenuation function.

* * * * *